March 22, 1960 E. S. BOERNER Plant Pat. 1,922
CHRYSANTHEMUM PLANT
Filed June 30, 1959
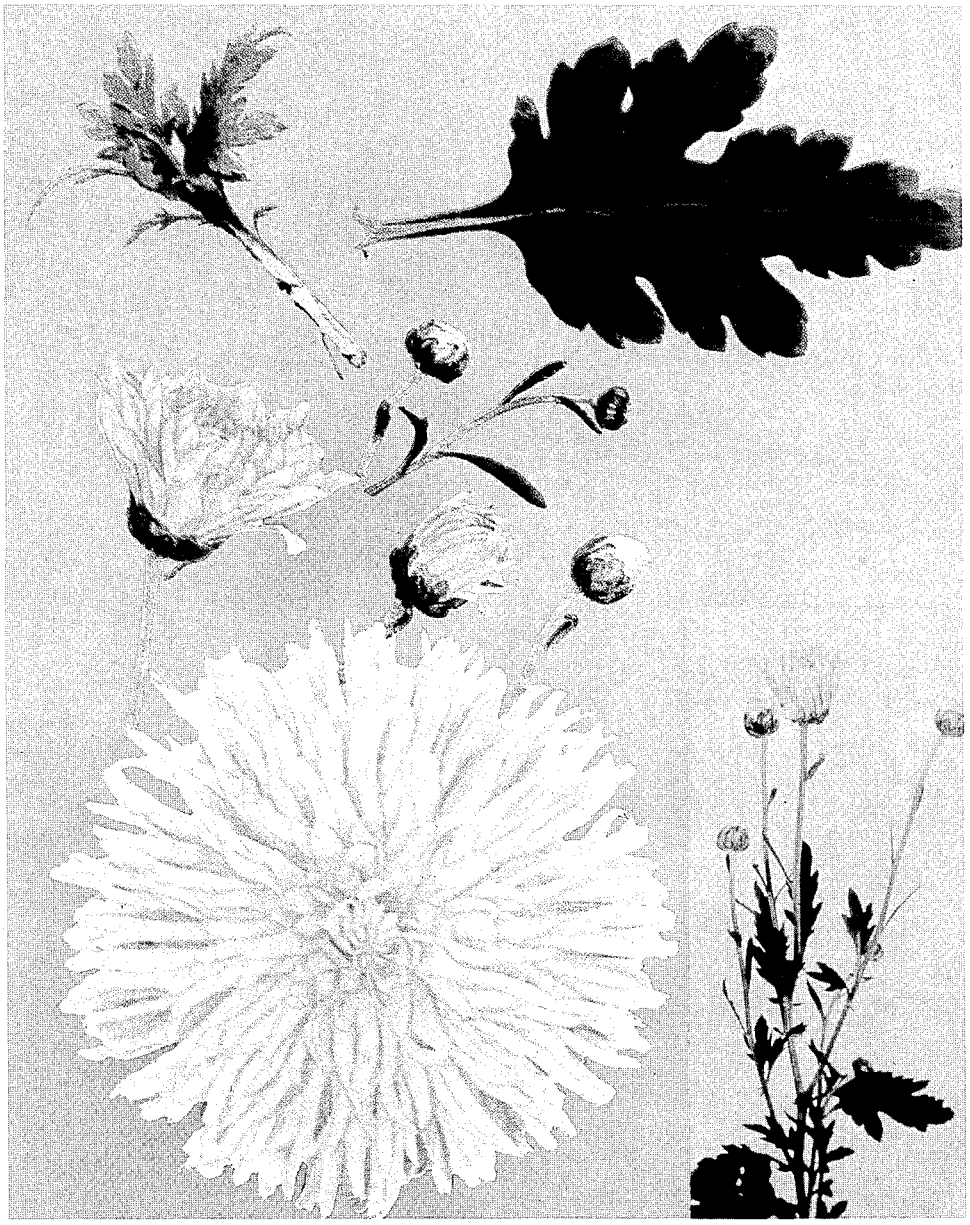
Inventor.
E. S. Boerner
By: Robbins & Robbins
Attorneys.

United States Patent Office

Plant Pat. 1,922
Patented Mar. 22, 1960

1,922

CHRYSANTHEMUM PLANT

Eugene S. Boerner, Newark, N.Y., assignor to Jackson & Perkins Company, Newark, N.Y., a corporation of New York Application June 30, 1959, Serial No. 824,143

1 Claim. (Cl. 47—60)

The present invention relates to a new an distinct variety of chrysanthemum plant of the shaggy decorative class, which was originated by me by crossing an unnamed and unpatented seedling, derived from a cross of "Flicker" (Plant Patent No. 1,465) × another unnamed and unpatented seedling of "Thrush" (Plant Patent No. 1,168) × "Seagull" (Plant Patent No. 1,130), with the variety "Cockatoo" (Plant Patent No. 1,171).

The primary objective of this breeding was to produce a new variety of chrysanthemum in which there is combined the general plant habits and shaggy flower form of the parent variety "Cockatoo" with a deep rich flower color. This objective was fully achieved, as evidenced by the following characteristics which are outstanding in the new variety and which distinguish it from its parents, as well as from all other varieties of which I am aware:

(1) An upright habit of growth;
(2) A shaggy flower form;
(3) Large flower size; and
(4) A distinctive Light Cadmium general color tonality of the flowers.

Asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, in the early morning during the first of October.

Parentage: Seedling.

*Seed parent.*—An unnamed seedling derived from a cross of "Flicker" × an unnamed seedling of "Thrush" × "Seagull."

*Pollen parent.*—"Cockatoo."

Classification: Shaggy decorative.

Growth: Tall; upright.

Cold resistance: Winter hardy and frost resistant in northern New York.

Blooming period: In the Newark, New York climatic area, average date of start of bloom is late September, with bloom continuing until frost.

*Flower*

(Observations made from specimens grown outdoors at Newark, New York, in the early morning during the first of October.)

Bud:

*Color.*—When sepals first divide—Empire Yellow, Plate 4. When petals begin to unfurl—Light Cadmium, Plate 4. When half-blown: inside of petals—Deep Chrome, Plate 3; outside of petals —Light Cadmium, Plate 4.

*Peduncle.* — Color — Absinthe Green, Plate 31. Strength—strong.

Bloom:

*Size.*—From 5 inches to 5½ inches.

*Stem.*—Strong; normal.

*Form.*—Shaggy decorative.

*Petalage.*—Double.

*Color.*—Center of flower—Deep Chrome, Plate 3. Outer petals—Empire Yellow, Plate 4. Base of petals—Light Green-yellow, Plate 5. Inside of petals—Light Cadmium, Plate 4. Reverse of petals—Pinard Yellow, Plate 4.

*Petals.*—Texture—waxy. Form—long; petals finish uneven and give an attractive ragged appearance.

*Fragrance.*—Characteristic chrysanthemum.

*Plant*

Form: Upright.

Growth: Free; vigorous.

Foliage:

*Size.*—Large.

*Quantity.*—Normal.

*Color.*—Upper side—Varley's Green, Plate 18. Under side—Cress Green, Plate 31.

*Texture.*—Leathery.

I claim:

A new and distinct variety of chrysanthemum plant of the shaggy decorative class, substantially as herein shown and described, characterized particularly as to novelty by the unique combination of an upright habit of growth, shaggy flower form, large flower size, and a distinctive Light Cadmium general color tonality of the flowers.

No references cited.